United States Patent [19]

Wilson et al.

[11] 4,212,994

[45] Jul. 15, 1980

[54] PROCESS FOR THE PREPARATION OF CARBOXYLIC ACID

[75] Inventors: David A. Wilson, Richwood; Roy W. Schmidt, Lake Jackson, both of Tex.

[73] Assignee: The Dow Chemical Company, Midland, Mich.

[21] Appl. No.: 921,685

[22] Filed: Jul. 3, 1978

[51] Int. Cl.² .............................................. C07C 51/02
[52] U.S. Cl. .................................... 562/568; 562/564; 562/565; 562/566; 562/572; 562/575
[58] Field of Search ............... 562/565, 566, 564, 568, 562/572, 575; 423/181

[56] References Cited

U.S. PATENT DOCUMENTS

| | | | |
|---|---|---|---|
| 3,439,026 | 4/1969 | Patton | 260/515 |
| 3,574,531 | 4/1971 | Schulz | 423/10 |
| 3,586,476 | 6/1971 | Beutner et al. | 423/395 |

OTHER PUBLICATIONS

Kunin, R., "Liquid Ion-Exchange Technology," Angew. Chem. Internat. Ed., vol. 1 (1962), 149–155.
Mogno, Yvon et al., "Extraction of Alkali and Alkaline Earth Metals by Dialkylphosphoric Acids," C. R. Acad. Sci., Paris, Ser. C (1968), 267(21), 1373–1376, (See Chem. Abstracts vol. 70 (1969) #100,207m.).
Kojima, Isao et al., "Extraction of Copper (II) and Sodium with Bis(2-Ethylhexyl) Hydrogen Phosphate," J. Inorg. Nucl. Chem. (1969) 31(6), 1815–1820, (See Chemical Abstracts, vol. 71 (1969), #25,157k).

*Primary Examiner*—Bernard Helfin
*Assistant Examiner*—L. Hendriksen
*Attorney, Agent, or Firm*—Michael L. Glenn

[57] ABSTRACT

A carboxylic acid is prepared by contacting an aqueous solution of the alkali metal or ammonium carboxylate with a liquid cation exchange agent dissolved in an organic solvent in which the carboxylic acid is substantially water immiscible. As an example, an aqueous solution of trisodium N-(2-hydroxyethyl)ethylenediaminetriacetate is contacted with di(2-ethylhexyl)phosphoric acid in kerosene to thereby form N-(2-hydroxyethyl)ethylenediaminetriacetic acid in the aqueous solution.

10 Claims, No Drawings

PROCESS FOR THE PREPARATION OF CARBOXYLIC ACID

BACKGROUND OF THE INVENTION

This invention relates to the preparation of a carboxylic acid from the corresponding alkali metal or ammonium carboxylate in an aqueous solution. In particular, this invention relates to the use of liquid ion exchange agents for the conversion of salts of carboxylic acids into the corresponding carboxylic acids.

Among the various methods previously used for the recovery of carboxylic acids from their salts, the most common has been acidification with an aqueous solution of a mineral acid. This method has not been entirely satisfactory for the recovery of water-soluble carboxylic acids or aminopolycarboxylic acids, which are chelating agents. The water-soluble carboxylic acids are difficult to separate from the salts of mineral acids.

The practice of this invention is useful to produce in high yield carboxylic acids free of contaminant by-product salts produced in the conventional acidification reactions.

SUMMARY OF THE INVENTION

The novel process comprises reacting by contacting an aqueous solution of an alkali metal or ammonium carboxylate with a liquid cation exchange agent in a substantially water-insoluble organic solvent which does not dissolve the carboxylic acid corresponding to the carboxylate, so as to effect acidification of said carboxylate to the corresponding carboxylic acid in an aqueous medium. The aqueous solution containing the carboxylic acid is then separated from the organic solvent.

The practice of the present invention embodies the discovery that despite the high alkalinity of solutions of ammonium or alkali metal carboxylates, liquid cation exchange agents effectively acidify these alkali metal carboxylates.

DETAILED DESCRIPTION OF THE EMBODIMENTS

The carboxylates acidified in the practice of this invention can be essentially any carboxylate which is soluble in water and which is substantially insoluble in the organic solvent for the liquid ion exchange agent. The practice of this invention is particularly applicable to alkali metal or ammonium salts of aliphatic hydroxycarboxylic acids or condensates thereof, for example, an alkali metal glycolate, an alkali metal salt of diglycolic acid, and the like. The practice of this invention is more particularly applicable to an alkali metal or ammonium salt of an iminopolycarboxylic acid or of an aminopolycarboxylic acid, such as alkali metal salts of nitrilotriacetic acid (NTA), ethylenediaminetetraacetic acid (EDTA), diethylenetriaminepentaacetic acid (DTPA), triethylenetetraaminehexaacetic acid (TTHA), hydroxyethyliminodiacetic acid (HEIDA), N,N-di(2-hydroxyethyl)glycine (DHEG), glycine, iminodiacetic acid (IDA), N-(2-hydroxyethyl)ethylenediaminetriacetic acid (HEDTA), and the like. The practice of this invention is most particularly applicable to those alkali metal salts of aminopolycarboxylic acid, such as DTPA and even more particularly HEDTA, which are likely to super-saturate rather than precipitate from a concentrated aqueous solution.

The term alkali metal carboxylate as used herein refers, generically, to ammonium carboxylate as well as lithium, potassium and sodium carboxylate and the like. The preferred alkali metal carboxylate is a sodium carboxylate.

It is operable to employ a mixture of alkali metal carboxylate compounds and in particular a variety of alkali metal ions in a single acidification. It is also operable in this process to employ a compound which bears carboxylic acid moieties as well as alkali metal carboxylate moieties. To illustrate, it is advantageous that the trisodium salt of HEDTA is the predominant species when acidification is initiated, but it is operable to initiate acidification when the trisodium, disodium or monosodium salt of HEDTA is the predominant species present. Of course, as the acidification progresses the predominant species is progressively one more highly acidified.

The carboxylic acid prepared by this method can bear alkali metal carboxylate moieties as well as carboxylic acid moieties. The only requirement is that the carboxylic acid is acidified to a greater degree than the alkali metal carboxylate from which it is prepared. However, it is desirable that the carboxylic acid is substantially completely acidified by this process.

The alkali metal carboxylates can be prepared by a variety of conventional means, for example reaction of esters with alkali metal hydroxides. U.S. Pat. Nos. 2,387,735 and 2,407,645 are of interest in that they describe methods of preparing sodium aminopolycarboxylates. Many alkali metal carboxylate compounds of interest are also available commercially.

The alkali metal carboxylate is present in an aqueous solution. The concentration of the alkali metal carboxylate is not critical. Advantageously, the alkali metal carboxylate is present in great enough concentration in the aqueous solution, so that the acidification can be conducted efficiently. Desirably, the aqueous product solution is of such concentration that it can be effectively and economically used as a chelating solution. Of course, the preferred range of alkali metal carboxylate concentration depends on the specific compound, but normally concentrations of from about 10 to about 50 weight percent are preferred.

The organic solvent should be liquid under conditions of use and inert to the liquid ion exchange agent, the alkali metal carboxylate and its corresponding acid. The organic solvent should also be insoluble in water (as classified in *The Handbook of Chemistry and Physics* or within the definition of insoluble as used by said handbook), so that a clean separation of the organic and the aqueous phases can be made after contact. Finally, the carboxylic acid product must be insoluble or substantially insoluble in the organic solvent to protect the yield of the acid product. Suitable organic solvents generally include kerosene, benzene, carbon tetrachloride, perchloroethylene and the like, with kerosene being the preferred solvent. Certain solvents, such as methylene chloride, are operable, but not desirable because of the poor separation effected between the organic and aqueous phases.

The liquid cation exchange agent can be any such agent which is insoluble or only slightly soluble in water and does not form emulsions with water and which reacts selectively with an alkali metal carboxylate to produce the corresponding carboxylic acid in the aqueous solution in high yield. Advantageously, the liquid cation exchange agent should be a phosphoric acid derivative corresponding to the formula

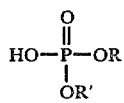

wherein each R and R' is independently hydrogen, alkyl, aralkyl, alkaryl or aryl. In general, it is desirable that R and R' are alkyl groups independently having from about 1 to about 20 carbon atoms. Generally, mixtures of operable liquid cation exchange agents can also be employed. Di(2-ethylhexyl)phosphoric acid (D2EHPA) is the preferred liquid cation exchange agent.

The concentration of the liquid cation exchange agent is not critical. However, the liquid cation exchange agent generally produces a higher degree of acidification for a given amount of the agent as the concentration of the agent in the organic solvent is increased. The aforementioned effect diminishes at higher concentrations of the agent. Of course, the preferred range of liquid cation exchange agent concentration depends on the specific agent, the organic solvent and the alkali metal carboxylate as well as other factors, but typically a concentration of the liquid cation exchange agent of from about 10 to about 70 percent by weight of the organic solution is preferred.

The aqueous solution of alkali metal carboxylate is contacted with the liquid ion exchange agent in the organic solution in any manner which produces a suitable transfer of ions from the aqueous to the organic phase. To illustrate, Kunin in *Angew. Chem.-Int'l Ed.*, 1:149–155(1963) discloses a variety of suitable liquid-liquid contactors. The contact can occur as a batch or a continuous process. Repeated contact of the alkali metal carboxylate with fresh portions of the liquid ion exchange agent can be used in a batchwise process to produce higher degrees of acidification. Advantageously, the contact can be effected by continuous countercurrent contact of the organic and aqueous phases in a suitable column contactor to promote substantially complete acidification with a minimal excess of liquid ion exchange agent.

The equivalent weight ratio of the liquid cation exchange agent to the alkali metal carboxylate is also important to the degree of acidification effected. When contact of the two reactants occurs in a batch operation, as opposed to a continuous operation, a relatively greater excess of the liquid cation exchange agent must be employed to achieve the same degree of acidification. An equivalent weight ratio (exchange agent:carboxylate) of less than 1:1 is operable, but not desirable because complete acidification is not effected. An equivalent weight ratio greater than 50:1 is operable, but not desirable even in a batch operation because of the diminishing increase in effectiveness at higher ratios and the uneconomic use of the exchange agent at these ratios.

The temperature during contact is not critical so long as the carboxylate and ion exchange reactants remain in their respective solutions and do not undergo significant decomposition. It is normally advantageous to contact the aqueous and organic solutions at a temperature of from about 20° C. to about 80° C., preferably from about 20° C. to about 50° C. However, a higher temperature may be desirable to prevent the acid product from prematurely precipitating.

Pressure during contact of from subatmospheric pressures to about 1000 pounds per square inch gauge (psig) is operable, with atmospheric pressure generally being preferred for reasons of convenience.

The degree of acidification can conveniently be determined from the measurement of the pH of the aqueous solution. The relative distribution of ionic species of the carboxylic acid in the solution can then be determined from the pertinent acid dissociation constants.

After the desired degree of acidification is effected, the aqueous phase containing the carboxylic acid can be separated from the organic phase by any convenient means known to the art. The separated organic phase can be extracted with fresh water to recover residual amounts of the carboxylic acid, but this is generally not necessary because of the low solubility of the acid in a properly selected organic solvent. Likewise, extraction of the separated aqueous phase with fresh organic solvent can be employed to remove residual impurities, but is generally not necessary.

The carboxylic acid product can be conveniently isolated by precipitating it from a hot, concentrated aqueous solution by cooling the solution. This method isolates the carboxylic acid substantially free of alkali metal carboxylates. Alternatively, the water can be evaporated or removed by distillation to isolate the carboxylic product as a residue. While the foregoing methods of recovering the acid product are convenient, the instant acidification process does not extend to and therefore is not limited by any particular method of product isolation.

When the liquid ion exchange agent is used in a large molar excess relative to the carboxylate, it can be used repeatedly prior to regeneration, because only a minor part of the agent present is exhausted in each acidification. The exchange agent can be regenerated in a batch or a continuous process by contacting the agent in the separated organic solution with a concentrated aqueous solution of a strong acid, such as hydrochloric acid, sulfuric acid and the like. Conveniently, in a batch process, an aqueous solution of a strong mineral acid is brought together and agitated with an equimolar or lesser amount of partially exhausted ion exchange agent in its organic solution, so as to regenerate the exchange agent. Alternatively, the partially exhausted liquid ion exchange agent in the organic solution can in a continuous process be contacted countercurrently with an aqueous solution of a strong mineral acid to effect regeneration of the liquid ion exchange agent. Desirably, the aqueous solution of mineral acid is employed in a concentration of at least 1 mole per liter. The partially exhausted exchange agent can be regenerated to greater than 95 percent of the acid form present in the fresh exchange agent by the aforementioned method. The regenerated exchange agent can be employed in the instant method of acidification.

The examples that follow further illustrate the invention, but are not to be taken as limiting its scope.

EXAMPLE 1

In a series of runs which differed only in the organic solvent, an aqueous solution containing 20 percent by weight of trisodium N-(2-hydroxyethyl)-ethylenediaminetriacetate (Na$_3$HEDTA) having a pH of 13.2 is brought together with an organic solution containing 40 percent by weight of D2EHPA to create a reaction mixture. This reaction mixture contains an equivalent weight ratio of D2EHPA to Na₃HEDTA of 10:1. The aqueous solution and organic solution are contacted with agitation at a temperature of about 22° C.

After one hour, the agitation is stopped and the organic and aqueous solutions are allowed to separate into phases. If the organic and aqueous phases are clearly defined and readily separable, the aqueous solution is separated from the organic solution. The pH of the aqueous solution is then measured.

The pH of the separated aqueous solution is adjusted to about 11.0 and the chelation value determined by titration with a standardized solution of calcium chloride in the presence of oxalate ions. The recovery of chelation value is calculated by comparing the total amount of chelant (as determined by the calcium titration) before reaction with the liquid ion exchange agent with the amount of chelant present in the separated aqueous phase after the reaction. The final pH and percent chelation recovery for contact with each of the organic solvents evaluated is tabulated in Table I.

TABLE I

| Solvent | Chelation Recovery (%) | Final pH |
|---|---|---|
| Kerosene | 99.6 | 3.55 |
| Carbon Tetrachloride | 98.2 | 3.63 |
| Perchloroethylene | 99.2 | 3.56 |
| Dichloromethane | * | 3.75 |

*Poor separation of phases, no titration made.

The pH data in Table I indicates that substantial acidification of the Na₃HEDTA occurs in all of the solvents. However, the pH of a saturated aqueous solution of HEDTA at 25° C. is about 2.2. Based on the acid dissociation constant of HEDTA, this batch process in kerosene, carbon tetrachloride and perchloroethylene completely acidifies about 20 percent of the Na₃HEDTA and produces essentially a remaining amount of the monosodium salt of HEDTA.

The recovery of chelation value in acidifications conducted with three of the solvents indicate that little of the Na₃HEDTA or the acidified products is lost to the organic phase. The methylene chloride solvent is less desirable than the other three solvents, because a clean separation between the phases is not obtained.

EXAMPLE 2

In a manner otherwise similar to the method set out in Example 1, a 20 weight percent solution of Na₃HEDTA is acidified with a variety of liquid cation exchange agents. In the tabulated separate runs, the aqueous solution of Na₃HEDTA is contacted with kerosene solutions of D2EHPA, oleic acid, or a 1:1 mixture by weight of D2EHPA and mono-2-ethylhexyl phosphoric acid (M2EHPA). In two more runs, dinonylnaphthalene sulfonic acid (DNNSA) in heptane is employed as the liquid cation exchange agent in the organic solvent. The final pH, the equivalent weight ratio of the exchange agent to Na₃HEDTA, weight percent of the agent in the organic solvent, and percent chelation recovery for contact with each of the exchange agents is tabulated in Table II.

TABLE II

| Exchange Agent | Eq. Ratio (Exch. Ag.:Na₃HEDTA) | % Conc. Exch. Agent | % Chelation Recovery | Final pH |
|---|---|---|---|---|
| D2EHPA | 2:1 | 40 | 97.9 | 4.6 |
| D2EHPA | 10:1 | 40 | 99.6 | 3.6 |
| Oleic Acid | 5:1 | 13 | —[1] | 7.2 |
| Oleic Acid | 10:1 | 13 | 90.0 | 7.4 |
| D2EHPA/M2EHPA | 1:1 | 43 | 80.2[2] | 4.7 |
| DNNSA | 1:1 | 20 | —[3] | —[3] |
| DNNSA | 10:1 | 20 | —[3] | —[3] |

[1] Very poor separation of layers; emulsion formed.
[2] Very slow phase separation.
[3] Loss of chelant into organic phase; emulsion formed.

The pH data in Table II indicates that the phosphoric acid derivatives are relatively more efficient exchange agents in this embodiment than are the other agents tested.

The recovery of chelation values with the four exchange agents tabulated indicates that D2EHPA is superior in this respect to the other liquid ion exchange agents.

EXAMPLE 3

An aqueous solution containing 20 percent by weight of Na₃HEDTA is brought together in separate acidifications with solutions of 10, 40 and 70 percent by weight D2EHPA in kerosene. The equivalent weight ratio of D2EHPA to Na₃HEDTA is varied for each concentration of D2EHPA in the ratios of 1:1, 2:1, 10:1 and 30:1. The manner of acidification is otherwise similar to that set out in Example 1. After the acidification the pH of the aqueous solution is measured. The equivalent weight ratio, weight percent of D2EHPA in kerosene and the final pH are tabulated in Table III.

TABLE III

| Equivalent Ratio (D2EHPA:Na₃HEDTA) | Final pH at Listed Concentration of D2EHPA | | |
|---|---|---|---|
| | 10% | 40% | 70% |
| 1:1 | 6.20 | 5.50 | 5.45 |
| 2:1 | 5.20 | 4.65 | 4.70 |
| 10:1 | 4.05 | 3.60 | 3.45 |
| 30:1 | 3.65 | 3.10 | 3.05 |

The pH data in Table III indicates that for a given equivalent weight ratio of D2EHPA to Na₃HEDTA, a greater degree of acidification is effected with 40 than with 10 weight percent D2EHPA. However, there is apparent only a slight increase in the degree of acidification when the concentration of D2EHPA is 70 instead of 40 weight percent. Further, the data in Table I indicates a significant increase in the degree of acidification at all concentrations of D2EHPA as the equivalent ratio of D2EHPA to Na₃HEDTA increases.

EXAMPLE 4

An aqueous solution containing 20 or 40 percent by weight of Na₃HEDTA is brought together in separate acidifications with solutions of 40 and 70 percent by weight D2EHPA in kerosene. The equivalent weight ratio of D2EHPA to Na₃HEDTA is 10:1 in each instance. The manner of acidification is otherwise similar to that set out in Example 1. After the acidification the pH of the aqueous solution is measured. The aqueous phase is then separated from the organic phase and the chelation value determined in the conventional manner. The initial weight percent of the Na₃HEDTA and of D2EHPA, the final pH of the aqueous solution and the recovery of chelation value are tabulated in Table IV.

TABLE IV

| $Na_3HEDTA$ (%) | D2EHPA (%) | Final pH | Recovery of Chelation Value (%) |
|---|---|---|---|
| 20 | 40 | 3.60 | 99.6 |
| 40 | 40 | * | 72.9 |
| 20 | 70 | 3.45 | 97.0 |
| 40 | 70 | * | 92.4 |

*Product crystallized before pH measurement obtained.

The data in Table IV indicates that at a concentration of 40 percent by weight $Na_3HEDTA$, the acid product formed precipitates very rapidly. This rapid precipitation results in the loss of some of the acid product on the separatory funnel, thereby resulting in a lower recovered chelation value. Separation at higher temperatures eliminates this problem.

EXAMPLE 5

An aqueous solution containing 20 percent by weight of $Na_3HEDTA$ and less than 2 parts per million (ppm) phosphorus by weight is brought together in separate acidifications at temperatures of 25° C. and 75° C. with a solution of 40 percent by weight D2EHP in kerosene. The equivalent weight ratio of D2EHPA to $Na_3HEDTA$ is 1:1 in each acidification. The manner of acidification is otherwise similar to that set out in Example 1. After 1 hour of contact the aqueous layer is separated from the organic phase and its pH is measured. The aqueous layer is then analyzed for phosphorus by conventional methods. The D2EHPA lost from the organic to the aqueous phase is estimated from the phosphorus analysis as a weight percent of that in the organic phase. The pertinent data is tabulated in Table V.

TABLE V

| Temperature (°C.) | Final pH | Phosphorus in $H_2O$ Layer (ppm) | Loss of D2EHPA* (%) |
|---|---|---|---|
| 25 | 5.30 | 29.9 | 0.037 |
| 75 | 5.45 | 30.5 | 0.040 |

*Assuming phosphorus is from D2EHPA.

The data in Table V demonstrates that very little of the D2EHPA, its sodium salt or hydrolysis product contaminates the HEDTA product in the aqueous layer.

EXAMPLE 6

A reciprocating plate column 6 feet in length and having a 1 inch internal diameter is used to effect continuous countercurrent contact of an aqueous solution of $Na_3HEDTA$ and a kerosene solution of D2EHPA. An aqueous solution containing 41.3 percent by weight $Na_3HEDTA$ is introduced into the top of the column. Into the bottom of the column is introduced a solution of kerosene containing 60 percent by weight D2EHPA. The rate of introduction of the two reactants is adjusted in separate runs to effect various equivalent weight ratios and various amounts of reactants put through the column in units of gallons per hour per square foot (gph/ft²). The strokes per minute of the reciprocating plate are optimized in each run to obtain the lowest pH measurement for the aqueous product stream. A final pH measurement of the aqueous product stream is taken at the end of the run. The column and solutions of reactants are heated in order to maintain the solubility of the acid within the reaction zone of the column. The relevant parameters and operating conditions are tabulated in Table VI.

TABLE VI

| Solution Throughput (gph/ft²) | Equivalent Ratio (D2EHPA/$Na_3HEDTA$) | Temperature (°C.) | Run Time (hours) | Final pH |
|---|---|---|---|---|
| 600 | 3.3:1 | 48 | 2.0 | 2.50 |
| 600 | 3.3:1 | 58 | 2.0 | 2.54 |
| 600 | 3.3:1 | 68 | 2.0 | 2.59 |
| 600 | 3.3:1 | 78 | 3.0 | 2.59 |
| 600 | 1.3:1 | 60 | 2.0 | 2.90 |
| 600 | 2.3:1 | 60 | 3.0 | 2.50 |
| 600 | 4.3:1 | 60 | 3.0 | 2.49 |
| 900 | 1.3:1 | 60 | 2.3 | 3.18 |
| 900 | 2.3:1 | 60 | 3.0 | 2.88 |
| 900 | 3.3:1 | 60 | 2.5 | 2.58 |
| 1200 | 3.3:1 | 60 | 2.8 | 2.83 |

At the lowest rate of solution throughput tested (600 gph/ft²), more than 60 percent of the $Na_3HEDTA$ is converted to HEDTA in all but one of the runs. The lower conversion effected in one of the runs can be attributed to the relatively slight excess of the liquid cation exchange agent employed in that instance. At higher rates of solution throughput an even greater excess of D2EHPA is necessary to effect the same degree of acidification.

Temperatures of from 48° C. to 78° C. have little effect on the degree of acidification effected.

Comparative Example 7

In a process not embodying the claimed process, an aqueous solution of $Na_3HEDTA$ is acidified with sulfuric acid. A 600-gram aqueous solution of 20.7 or 41.3 weight percent $Na_3HEDTA$ is cooled to 0° C. Sulfuric acid is then added to the aqueous solution to reduce the pH of the solution to 2.0. The solution is then seeded with a small amount of sodium sulfate crystals to precipitate solids. The solution is filtered by suction. The remaining solids are washed with distilled water at 0° C. and this second filtrate is collected. Each filtrate is analyzed to measure the weight percent of sulfate and the percent recovery of chelation value by conventional methods. The data and operating conditions are tabulated in Table VII.

TABLE VII

| $Na_3HEDTA$ (Weight %) | $H_2O$ Wash (milliliters) | Filtrate 1 | | Filtrate 2 | |
|---|---|---|---|---|---|
| | | Chelation (% Recovery) | Sulfate (Weight %) | Chelation (% Recovery) | Sulfate (Weight %) |
| 41.3 | 500 | 29 | 19.4 | 20 | 10.7 |
| 20.7 | 175 | 73.5 | 21.5 | 23.5 | 13.4 |

As is seen from the data in Table VII, the solubility of sodium sulfate is high enough that a large amount remains in the solutions of HEDTA. Therefore, it is difficult to separate the water-soluble carboxylic acid product from the salt of the mineral acid.

What is claimed is:

1. A process for preparing a carboxylic acid from its corresponding alkali metal-type carboxylate, comprising the steps of:
   (a) reacting by contacting an aqueous solution of the alkali metal or ammonium carboxylate with a liquid cation exchange agent in a substantially water-insoluble organic solvent which does not dissolve the corresponding carboxylic acid, said liquid cation exchange agent corresponding to the formula

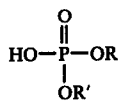

wherein R and R' are each independently hydrogen, alkyl, aralkyl, alkaryl or aryl with the proviso that the total number of carbon atoms in R plus R' is at least equal to the integer 1, so as to effect acidification of the carboxylate to the corresponding carboxylic acid in the aqueous medium; and
   (b) separating the aqueous solution containing the carboxylic acid from the organic solvent.

2. The process as described in claim 1 wherein the carboxylic acid prepared is substantially completely acidified.

3. The process as described in claim 1 wherein said carboxylate is a sodium carboxylate.

4. The process as described in claim 1 wherein the liquid cation exchange agent is di(2-ethylhexyl)phosphoric acid.

5. The process as described in claim 4 wherein the water-insoluble organic solvent is kerosene.

6. The process as described in claim 5 wherein said carboxylate is a trialkali metal salt of N-(2-hydroxyethyl)ethylenediaminetriacetic acid.

7. A process for preparing N-(2-hydroxyethyl)ethylenediaminetriacetic acid from trisodium N-(2-hydroxyethyl)ethylenediaminetriacetate, comprising the steps of:
   (a) reacting by contacting at a temperature of from about 20° C. to about 80° C. an aqueous solution containing from about 10 to about 50 weight percent of trisodium N-(2-hydroxyethyl)ethylenediaminetriacetate (Na₃HEDTA) with a kerosene solution containing from about 10 to about 70 weight percent of di(2-ethylhexyl)phosphoric acid (D2EHPA), so as to effect an equivalent weight ratio of D2EHPA to Na₃HEDTA of from 1:1 to 50:1; and
   (b) separating the aqueous solution containing the N-(2-hydroxyethyl)ethylenediaminetriacetic acid from the kerosene solution.

8. The process as described in claim 7 wherein contact between the D2EHPA and the Na₃HEDTA is effected countercurrently in a continuous process.

9. The process as described in claim 8 further comprising the steps of regenerating the D2EHPA after contact with the Na₃HEDTA by contacting it in a continuous countercurrent process with an aqueous solution of a strong mineral acid and recycling the regenerated D2EHPA to step (a).

10. The process as described in claim 5 wherein said carboxylate is an alkali metal or ammonium salt of an iminopolycarboxylic acid or an aminopolycarboxylic acid.

* * * * *